United States Patent
Sato et al.

(10) Patent No.: US 6,613,850 B1
(45) Date of Patent: Sep. 2, 2003

(54) METHOD FOR FEEDING BORON COMPOUNDS, FINE PARTICLES OF BORON COMPOUNDS, CATALYST COMPONENTS FOR THE POLYMERIZATION OF OLEFINS COMPRISING THEM, AND PROCESSES FOR THE PRODUCTION OF THE PARTICLES

(76) Inventors: Hideki Sato, 2-6-445, Ikku-cho, Niihama-shi, Ehime, 792-0025 (JP); Hiroaki Katayama, 98-4203, Daijuku, Sodegaura-shi, Chiba, 299-0241 (JP); Kazuki Wakamatsu, 6-11-13, Naguraekimae, Sodegaura-shi, Chiba, 299-0246 (JP)

(*) Notice: Subject to any disclaimer, the term of this patent is extended or adjusted under 35 U.S.C. 154(b) by 0 days.

(21) Appl. No.: 09/125,518

(22) PCT Filed: Dec. 19, 1997

(86) PCT No.: PCT/JP97/04716
§ 371 (c)(1),
(2), (4) Date: Nov. 23, 1998

(87) PCT Pub. No.: WO98/28343
PCT Pub. Date: Jul. 2, 1998

(30) Foreign Application Priority Data

Dec. 20, 1996 (JP) .............................. 8-341988
Jan. 14, 1997 (JP) .............................. 9-005033
Jan. 14, 1997 (JP) .............................. 9-005034
Jul. 4, 1997 (JP) .............................. 9-179693

(51) Int. Cl.⁷ .............................. C08F 4/44; C08F 4/14
(52) U.S. Cl. ...................... 526/133; 526/134; 526/195; 502/104; 502/202; 502/203
(58) Field of Search ................... 526/133, 134, 526/195; 556/7, 8; 568/6; 502/104, 202, 203

(56) References Cited

U.S. PATENT DOCUMENTS

| | | | |
|---|---|---|---|
| 3,726,968 A | 4/1973 | Loomans | |
| 4,410,450 A | 10/1983 | Sasaki et al. | |
| 5,064,802 A | 11/1991 | Stevens et al. | 502/155 |
| 5,321,106 A | 6/1994 | LaPointe | 526/126 |
| 5,399,781 A | 3/1995 | Doellein | |
| 5,408,017 A | 4/1995 | Turner et al. | 526/134 |
| 5,414,181 A | 5/1995 | Bearden, Jr. et al. | |
| 5,420,355 A * | 5/1995 | Ikeda et al. | 568/6 |
| 5,427,991 A | 6/1995 | Turner | |
| 5,493,056 A | 2/1996 | Ikeda et al. | 568/8 |
| 5,510,536 A | 4/1996 | Ikeda et al. | |
| 5,545,759 A | 8/1996 | Ikeda et al. | 568/8 |
| 5,600,003 A | 2/1997 | Baur et al. | |
| 5,600,005 A | 2/1997 | Naganuma et al. | |
| 5,693,867 A | 12/1997 | Baur et al. | |
| 5,939,347 A * | 8/1999 | Ward et al. | 502/104 |

FOREIGN PATENT DOCUMENTS

| | | |
|---|---|---|
| EP | 0 604 963 A1 | 7/1994 |
| EP | 0 609 452 A | 8/1994 |
| EP | 0 612 769 A2 * | 8/1994 |
| EP | 0 634 416 A1 * | 1/1995 |
| EP | 0 662 478 A1 | 7/1995 |
| EP | 0 842939 A1 | 5/1998 |
| JP | WO/94 00459 | 1/1994 |
| JP | 6-157782 | 6/1994 |
| WO | WO/88 05793 | 8/1988 |
| WO | WO 93/11172 * | 6/1993 |
| WO | WO 94/07928 * | 4/1994 |

* cited by examiner

*Primary Examiner*—David W. Wu
*Assistant Examiner*—B. Harlan

(57) ABSTRACT

A method for feeding a boron compound, which comprises feeding at least one boron compound selected from (1) to (3) described below in the state suspended or slurried in a solvent continuously to a reactor; a boron compound in the form of fine particles being one or more boron compounds selected from (1) to (3) described below and having a maximum particle diameter of 50 μm or less; a catalyst component for olefin polymerization consisting of said boron compound in the form of fine particles; a method for producing a boron compound in the form of fine particles which comprises dissolving one or more boron compounds selected from (1) to (3) described below in an aromatic hydrocarbon solvent and then precipitating in an aliphatic hydrocarbon solvent; and a method for producing a boron compound in the form of fine particles which comprises pulverizing one or more boron compounds selected from (1) to (3) described below so that their maximum particle diameter is 50 μm or less. (1) a boron compound represented by the general formula: $BQ^1Q^2Q^3$, (2) a boron compound represented by the general formula: $G^+(BQ^1Q^2Q^3Q^4)^-$, and (3) a boron compound represented by the general formula: $(L\text{-}H)^+(BQ^1Q^2Q^3Q^4)^-$.

23 Claims, No Drawings

METHOD FOR FEEDING BORON COMPOUNDS, FINE PARTICLES OF BORON COMPOUNDS, CATALYST COMPONENTS FOR THE POLYMERIZATION OF OLEFINS COMPRISING THEM, AND PROCESSES FOR THE PRODUCTION OF THE PARTICLES

This application is the national phase under 35 U.S.C. §371 of prior PCT International Application No. PCT/JP97/04716 which has an International filing date of Dec. 19, 1997 which designated the United States of America, the entire contents of which are hereby incorporated by reference.

TECHNICAL FIELD

The present invention relates to a method for feeding a specific boron compound to a reactor, a boron compound having a controlled particle diameter useful as a component of a catalyst for polymerization of an olefin and a method for producing the same. More particularly, it relates to a method for continuously feeding a boron compound useful as a component of a catalyst for polymerization of an olefin to a reactor, particularly an apparatus for preparing a catalyst or a reactor for polymerization of an olefin, said boron compound having a controlled particle diameter, and a method for producing said boron compound.

BACKGROUND ART

Many reports have already been presented on methods for producing olefin polymers with catalysts for olefin polymerization, which uses a transition metal compound (e.g. a metallocene complex or non-metallocene complex) and a specific boron compound. Said boron compound, which is also commercially available in recent years, is usually solid containing large size particles having a particle diameter of several hundreds micrometers to several millimeters, and while it is soluble in toluene to some extent, it has a low solubility in most solvents including saturated hydrocarbons. Therefore, conventionally it has been used in a solution having not so high concentration or used by adding undissolved part of said boron compound remaining in solid form into a vessel.

For example, In Japanese Patent Publication (Kohyo) No. Hei 1-502036 discloses a method for producing an olefin polymer in which tri-n-butylammonium tetrakis(phenyl)borate is suspended in toluene, bis(pentamethylcyclopentadienyl) zirconium dimethyl is added thereto, $Cp^*_2Zr(C_6H_4)B(C_6H_5)_3$ <<wherein Cp* represents $\eta^5$-pentamethylcyclopentadienyl group>> is isolated and used as a catalyst for polymerization of an olefin. In this method, tri-n-butylammonium tetrakis(phenyl)borate is provided in advance in the form of a suspension in toluene in a reactor for preparing a catalyst, and the catalyst is prepared by adding a metallocene complex thereto.

In addition, in U.S. Pat. No. 5,408,017, it is disclosed that a method for producing an olefin polymer in a high-pressure polymerization apparatus at 1,300 bar, in which method N,N-dimethylanilnium tetrakis(pentafluorophenyl)borate and dimethylsilylbis(4,5,6,7-tetrahydroindenyl) zirconium dimethyl are mixed in toluene to prepare a homogeneous catalyst solution, which is used as a catalyst for polymerization of an olefin. In this method, while a solid N,N-dimethylanilnium tetrakis(pentafluorophenyl)borate is used for the preparation of the catalyst, a homogeneous catalyst solution is provided before use for polymerization by mixing it with the metallocene complex in toluene, and then said solution is continuously fed to a polymerization reactor with a high-pressure pump.

Furthermore, Japanese Patent Publication (Kokai) No. Hei 7-157508 discloses a method in which a solution of triisobutyl aluminum in toluene is added to a solution of diphenylmethylene (cyclopentadienyl) (fluorenyl) zirconium dichloride in toluene in a separate vessel before use for polymerization, and further, a solution of N,N-dimethylanilnium tetrakis(pentafluorophenyl)borate in toluene is added to obtain a homogeneous catalyst solution, then said solution is fed to a high-temperature high-pressure polymerization reactor.

Conventionally, as described above, when said boron compound is continuously fed to a reactor, a discontinuous procedure for preparing a homogeneous catalyst solution in a separate vessel, was adopted or a solution having not so high concentration was used.

In Published Specification No. WO94/00459, there is described a method for producing said boron compound and a method for purifying a produced crude boron compound that is colored. According to said method for purification, a method is disclosed in which the produced crude boron compound dissolved in ethers, alcohols, ketones or halogenated aliphatic hydrocarbons as a solvent is precipitated by water or an aliphatic hydrocarbon solvent, but there is no description for particle diameter of the obtained boron compound.

DISCLOSURE OF INVENTION

In view of these circumstances, the problem to be solved by the present invention, in other words, the purpose of the present invention is to provide a method capable of feeding a boron compound useful as a catalyst component for polymerization of an olefin continuously and in large amount to a reactor, and additionally, to provide a boron compound capable of allowing steady feed thereof without using it in the state of a solution and allowing stable operation of a feeding apparatus, when used as a catalyst component for polymerization of olefin or the like, and to provide a method for producing said boron compound.

Namely, the present invention relates to a method for feeding a boron compound, which comprises feeding at least one boron compound selected from (1) to (3) described below in the state suspended or slurried in a solvent continuously to a reactor; a boron compound in the form of fine particles having a maximum particle diameter of 50 $\mu$m or less comprising one or more boron compounds selected from (1) to (3) described below; a catalyst component for olefin polymerization consisting of said boron compound in the form of fine particles; a method for producing a boron compound in the form of fine particles which comprises dissolving one or more boron compounds selected from (1) to (3) described below in an aromatic hydrocarbon solvent and then precipitating in an aliphatic hydrocarbon solvent; and a method for producing boron compound in the form of fine particles, which comprises pulverizing one or more boron compounds selected from (1) to (3) described below so that their maximum particle diameter is 50 $\mu$m or less.

(1) a boron compound represented by the general formula: $BQ^1Q^2Q^3$, (2) a boron compound represented by the general formula: $G^+(BQ^1Q^2Q^3Q^4)^-$, and (3) a boron compound represented by the general formula: $(L-H)^+(BQ^1Q^2Q^3Q^4)^-$ (in each of the above general formulae, B is a boron atom in the trivalent valence state, $Q^1$ to $Q^4$ are a halogen atom, a hydrocarbon group, a halogenated hydrocarbon group, a substituted silyl group, an alkoxy group or a di-substituted amino group, which may be the same or different, respectively. $G^+$ is an inorganic or organic cation, L is a neutral Lewis base, and $(L-H)^+$ is a Brønsted acid.)

The present invention is described below in more detail.

The boron compound used in the present invention is at least one boron compound selected from (1) to (3) described below.

(1) a boron compound represented by the general formula: $BQ^1Q^2Q^3$, (2) a boron compound represented by the general formula: $G^+(BQ^1Q^2Q^3Q^4)^-$, and (3) a boron compound represented by the general formula: $(L-H)^+(BQ^1Q^2Q^3Q^4)^-$ (in each of the above general formulae, B is a boron atom in the trivalent valence state, $Q^1$ to $Q4$ are a halogen atom, a hydrocarbon group, a halogenated hydrocarbon group, a substituted silyl group, an alkoxy group or a di-substituted amino group, which may be the same or different, respectively. $G^+$ is an inorganic or organic cation, L is a neutral Lewis base, and $(L-H)^+$ is a Brønsted acid.)

In the boron compound (1) represented by the general formula: $BQ^1Q^2Q^3$, B is a boron atom in the trivalent valence state, $Q^1$ to $Q^3$ are a halogen atom, a hydrocarbon group, a halogenated hydrocarbon group, a substituted silyl group, an alkoxy group or a di-substituted amino group, which may be the same or different, respectively. $Q^1$ to $Q^3$ are preferably a halogen atom, a hydrocarbon group containing 1–20 carbon atoms, a halogenated hydrocarbon group containing 1 to 20 carbon atoms (for example, a fluorinated aryl group of 6 to 20 carbon atoms containing at least one fluorine atom being preferred), a substituted silyl group containing 1 to 20 carbon atoms, an alkoxy group containing 1 to 20 carbon atoms or an amino group containing 2 to 20 carbon atoms, and more preferred $Q^1$ to $Q^3$ are a halogen atom, a hydrocarbon group containing 1 to 20 carbon atoms, or a halogenated hydrocarbon group containing 1 to 20 carbon atoms.

Specific examples of the boron compound (1) represented by the general formula: $BQ^1Q^2Q^3$ include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane and the like, with tris(pentafluorophenyl)borane being the most preferred.

In the boron compound (2) represented by the general formula: $G^+(BQ^1Q^2Q^3Q^4)$, $G^+$ is an inorganic or organic cation, B is a boron atom in the trivalent valence state, and $Q^1–Q^4$ is the same as $Q^1$ to $Q^3$ described in (1) above.

In specific examples of the boron compound (2) represented by the general formula: $G^+(BQ^1Q^2Q^3Q^4)^-$, inorganic cations as $G^+$ include ferrocenium cation, alkyl-substituted ferrocenium cation, silver cation and the like, and organic cations as $G^+$ include triphenylmethyl cation and the like. Particularly preferred one as $G^+$ is carbenium cation and the most preferred one is triphenylmethyl cation. $(BQ^1Q^2Q^3Q^4)^-$ includes tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluorophenyl)borate, tetrakis(3,5-bistrifluoromethylphenyl)borate and the like.

Specific combinations of them include ferrocenium tetrakis(pentafluorophenyl)borate, 1,1'-dimethylferrocenium tetrakis(pentafluorophenyl)borate, silver tetrakis (pentafluorophenyl) borate, triphenylmethyl tetrakis(pentafluorophenyl)borate, triphenylmethyl tetrakis(3,5-bistrifluoromethylphenyl)borate and the like, and triphenylmethyl tetrakis(pentafluorophenyl) borate is most preferable.

In the boron compound (3) represented by the general formula: $(L-H)^+(BQ^1Q^2Q^3Q4)^-$, L is a neutral Lewis base, $(L-H)^+$ is a Brønsted acid, B is a boron atom in the trivalent valence state, and $Q^1$ to $Q^4$ is the same as $Q^1$ to $Q^3$ described in (1) above.

In specific examples of the boron compound (3) represented by the general formula: $(L-H)^+(BQ^1Q^2Q^3Q^4)^-$, $(L-H)^+$ as the Brønsted acid includes trialkyl-substituted ammonium, N,N-dialkylanilinium, dialkylammonium, triarylphosphonium and the like, and $(BQ^1Q^2Q^3Q4)^-$ includes those mentioned above.

Specific combinations thereof include triethylammonium tetrakis(pentafluorophenyl)borate, tripropylammonium tetrakis(pentafluorophenyl)borate, tri-n-butylammonium tetrakis(pentafluorophenyl)borate, tri(n-butyl)ammonium tetrakis (3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl) phosphonium tetrakis(pentafluorophenyl) borate, tri(dimethylphenyl)phosphonium tetrakis (pentafluorophenyl) borate and the like, and tri-n-butylammonium tetrakis (pentafluorophenyl)borate or N,N-dimethylanilinium tetrakis(pentafluorophenyl)borate is most preferable.

The boron compound used in the present invention is preferably the boron compounds of (2) or (3) described above and in particular preferably triphenylmethyl tetrakis (pentafluorophenyl)borate and N,N-dimethylanilinium tetrakis(pentafluorophenyl)borate. Most preferably, it is N,N-dimethylanilinium tetrakis(pentafluorophenyl)borate.

In the present invention, the above described boron compound is used in the state suspended or slurried in a solvent. The state suspended or slurried in a solvent referred to in the present invention means the state in which solids are not completely dissolved in the solvent and solid particles are dispersed in the solvent. In the present invention, the state of suspension and the state of slurry are not particularly distinguished.

In the present invention, when the above described boron compound is fed in the state of which the boron compound is suspended or slurried in a solvent, it is preferred that the sedimentation velocity of said boron compound in the suspended or slurried state is lower than the flow velocity in the pipeline in order that, for example, said boron compound does not deposit in the pipeline.

In the present invention, the solvent used for suspending or slurrying is not particularly limited insofar as it does not cause problems in the use of the boron compounds, and hydrocarbon solvents are preferably used.

As the hydrocarbon solvents, either saturated hydrocarbon solvents or aromatic hydrocarbon solvents may be used, but saturated hydrocarbon solvents are preferred from the viewpoint of problems such as offensive smell, in the field of polymerization of olefins. The saturated hydrocarbon solvents include butane, hexane, heptane, octane, cyclohexane, dodecane, liquid paraffin and the like, and the aromatic hydrocarbon solvents include benzene, toluene, xylene and the like.

In the present invention, it is preferred to use a solvent having a high viscosity in order that the sedimentation velocity of said boron compound in the suspended or slurried state is lower than the flow velocity in the pipeline. The viscosity of the solvent is preferably 0.8 cp (centipoise) or more, more preferably 1.4–1200 cp, most preferably 1.6–50 cp.

Specific examples of solvents having a high viscosity include dodecane, various liquid paraffins, mixed solvents of these with other solvents and the like. As the liquid paraffins, for example, commercially available liquid paraffins having various viscosities within about 2 to about 2000 cp can be used. The viscosity referred to herein means the viscosity at 20° C.

When a pipeline is used in the feeding method of the present invention, the diameter of the pipeline is not particularly limited and is 0.5 to 100 mm, preferably 1 to 50 mm and more preferably 1.5 to 30 mm.

In the present invention, there is no particular limitation in the ratio between the amount to be used of the boron compound in the state of which said boron compound is suspended or slurried in a solvent and that of the solvent. While the above described boron compound is soluble to some extent in the aromatic hydrocarbon solvent such as toluene, according to the present invention in which the undissolved part is used in the suspended or slurried state, it is possible to feed a large amount of the boron compound in smaller volume. In addition, while the above described boron compound has a low solubility in the saturated hydrocarbon solvent and said boron compound contained in the solution are small in amount, according to the present invention, it is possible to feed a large amount of said boron compound in smaller volume.

When an aromatic hydrocarbon solvent is used, it is possible to feed in the ratio between the above described boron compound and the solvent, represented by a molar number of the boron compound to the volume of the solvent, of 2–800 millimoles/liter, and it is possible to feed more preferably in 6–500 millimoles/liter and further preferably 10–300 millimoles/liter. When a saturated hydrocarbon solvent is used, it is possible to feed in the ratio of 0.0001–800 millimoles/liter, and it is possible to feed more preferably in 0.001–500 millimoles/liter.

In the present invention, the above described boron compound is continuously fed to a reactor in the state of which the boron compound is suspended or slurried in a solvent.

The reactor herein refers to an apparatus subjected to the reaction using the above described boron compound, and include, for example, catalyst preparation apparatuses in which the above described boron compound is continuously fed in a large scale to and reacted with a transition metal compound such as a metallocene complex, non-metallocene complex or the like, and a reactors for olefin polymerization. Among them, it is applied suitably from the industrial viewpoint to reactors for olefin polymerization to which the above described boron compound needs to be continuously fed for a long period.

The reactors for olefin polymerization include, for example, reactors used for solvent polymerization or slurry polymerization in which an aliphatic hydrocarbon such as butane, pentane, hexane, heptane, octane or the like is used as the solvent, high-pressure ionic polymerization carried out without solvent and under high-temperature and high-pressure, gas phase polymerization carried out in a gaseous monomer and the like.

Preferred one is a reactor for olefin polymerization by high-temperature solution polymerization in which the polymerization of olefins is carried out using a solvent such as cyclohexane or the like under conditions of 120–250° C. and 5–50 kg/cm$^2$ at which polymers are melted or by high-pressure ionic polymerization in which the polymerization is carried out under a pressure of at least 300 kg/cm$^2$G and a temperature of at least 130° C. More suitably, it can be applied to a reactor for olefin polymerization by high-pressure ionic polymerization in which feed needs to be continued for a long period, and the advantage of the present invention is especially great.

In the present invention, when the above described boron compound are continuously fed to a reactor in the state suspended or slurried in a solvent, the feed to the reactor is suitably effected using a pump through a pipeline.

In the present invention, while shape, particle property, particle diameter, distribution of particle size and the like of the above described boron compounds are not particularly limited, it is preferred that the particle diameter is smaller because the possibility of blockade in a feeding apparatus (for example, pump) is reduced and the sedimentation velocity in the pipeline tends to become lower.

Such boron compounds include the above described boron compounds in the form of fine particles having a maximum particle diameter of 50 μm or less. Such boron compounds in the form of fine particles allow steady feed by and stable operation of the feeding apparatus, without any troubles such as blockade in the feeding apparatus (for example, pump) in case where used in the industrial production conducted in a large scale, by using, for example, in the suspended or slurried state or in the powdery state rather than the dissolved state, when, for example, used as a catalyst component for olefin polymerization. The maximum particle diameter of such boron compounds in the form of fine particles is preferably 30 μm or less, more preferably 10 μm or less and in particular preferably 5 μm or less.

A method for producing such boron compounds in the form of fine particles is not particularly limited insofar as it allows the maximum particle diameter of the boron compounds to be 50 μm or less, and there can be illustrated, for example, a method in which the above described boron compound is dissolved in an aromatic hydrocarbon solvent and then precipitated in an aliphatic hydrocarbon solvent, or the like.

Specific examples of said aromatic hydrocarbon solvent include benzene, toluene, ethylbenzene, propylbenzene, isopropylbenzene, butylbenzene, isobutylbenzene, o-xylene, m-xylene, p-xylene, 1,2,3-trimethylbenzene, 1,2,4-trimethylbenzene, 1,3,5-trimethylbenzene, fluorobenzene, o-difluorobenzene, m-difluorobenzene, p-difluorobenzene, 1,2,3-trifluorobenzene, 1,2,4-trifluorobenzene, 1,3,5-trifluorobenzene, 1,2,3,4-tetrafluorobenzene, 1,2,4,5-tetrafluorobenzene, pentafluorobenzene, hexafluorobenzene, chlorobenzene, o-dichlorobenzene, m-dichlorobenzene, p-dichlorobenzene, 1,2,3-trichlorobenzene, 1,2,4-trichlorobenzene, 1,3,5-trichlorobenzene, 1,2,3,4-tetrachlorobenzene, 1,2,4,5-tetrachlorobenzene, pentachlorobenzene, hexachlorobenzene, bromobenzene, o-dibromobenzene, m-dibromobenzene, p-dibromobenzene, 1,2,3-tribromobenzene, 1,2,4-tribromobenzene, 1,3,5-tribromobenzene, 1,2,3,4-tetrabromobenzene, 1,2,4,5-tetrabromobenzene, pentabromobenzene, hexabromobenzene and the like. Preferred one is toluene.

Usually, it is desirable that the concentration of the solution of said boron compound is at the solubility for saturation. It is also preferable to set the temperature of the solution higher in order to increase the concentration.

Specific examples of the above described aliphatic hydrocarbon solvent include pentane, 2-methylpentane, 3-methylpentane, cyclopentane, methylcyclopentane, hexane, 2-methylhexane, 3-methylhexane, cyclohexane, methylcyclohexane, heptane, 2-methylheptane, 3-methylheptane, 4-methylheptane, cycloheptane, octane, nonane, decane, a petroleum ether (petroleum benzine), a mineral oil (paraffin oil), ligroin (mineral spirit) and the like, and hexane or heptane is preferred.

The method for precipitating the boron compound from an aromatic hydrocarbon solution to an aliphatic hydrocarbon solvent includes, generally, a method in which the solution is added dropwise to a large amount of stirred aliphatic hydrocarbon solvent.

The rate of dropwise addition can be set at any value according to the amount of the solution.

The method of stirring during the dropwise addition includes a method in which the known stirring blade is used for stirring, a method in which one of various dispersing instruments excellent in dispersing efficiency (for example, homogenizer, line mixer, ultrasonic radiator and the like), and any known method can be applied without particular limitation.

Depending on particular case, the stirring may be completely omitted.

The amount of the aliphatic hydrocarbon solvent to be used is not particularly limited and any amount of the aliphatic hydrocarbon solvent required to precipitate the boron compounds dissolved in an aromatic hydrocarbon solvent may be used. Specifically, the aliphatic hydrocarbon solvent may be used in an amount 0.1 to 1,000 times the volume or weight of the solution of the boron compound in the aromatic hydrocarbon solvent. More preferably, it is used in an amount 1 to 100 times, further preferably 1 to 10 times.

Sometimes, the obtained boron compound in the form of fine particles is washed further with an aliphatic hydrocarbon solvent.

The boron compound in the form of fine particles obtained in the above described manner can be those having a maximum particle diameter of 10 $\mu$m or less, and is substantially free from the aromatic hydrocarbon solvent such as toluene or the like.

And, as the method for producing such a boron compound in the form of fine particles, there is given a method in which it is converted into fine particles having the maximum particle diameter of 50 $\mu$m or less by pulverization.

The method for pulverization is not particularly limited insofar as it is a pulverizing method allowing to pulverize said boron compounds into those of the maximum particle diameter of 50 $\mu$m or less, and may be any one of batch pulverizing method and continuous pulverizing method using routine pulverizing machine, or closed circuit pulverization method in which classification is simultaneously performed.

Specific examples of such pulverizing machine include jaw crusher, gyratory crusher, hammer crusher, roll crusher, ring roller mill, ball bearing mill, bowl mill, edge runner, stamp mill, hammer mill, cage mill, pin mill, disintegrator, dismembrator, cutter mill, feather mill, oscillating rod mill, aerofall mill, cascade mill, hard shell mill, turbo-mill, microcyclomate, hurricane mill, pot mill, compound mill, compartment mill, conical ball mill, supercritical mill, radial mill, tower mill, circular vibration mill, disk mill, high swing ball mill, centrifugal ball mill, sand grinder, atomizer, pulverizer, supermicron mill, jet mill, colloid mill, mortar and the like.

The method for pulverization may either be a dry pulverizing method which is carried out with the boron compound in dry state or wet pulverizing method which is carried out using a solvent or dispersing medium depending on the kind of pulverizing machine. A preferable solvent or dispersing medium used in the wet pulverizing method is an aliphatic hydrocarbon solvent.

As the aliphatic hydrocarbon solvent, similar one to the already described aliphatic hydrocarbon solvent can be used.

The method for controlling the particle diameter of the boron compound by pulverization is not particularly limited in either a dry pulverizing method and a wet pulverizing method, and may be one which allows pulverization by selecting conditions for pulverization such that the maximum particle diameter of the boron compounds is 50 $\mu$m or less. The conditions for pulverization include, for example, pulverization time, pulverization temperature, number of vibration of pulverizing machine, number of rotation, flow rate of gas or liquid applied to pulverizing machine, flow velocity, slurry concentration of slurry of the boron compounds when wet pulverization is conducted, and the like, but the conditions are not limited to them. Similarly, by selecting conditions for pulverization, the maximum particle diameter of the boron compounds can be controlled to 30 $\mu$m or less, 10 $\mu$m or less or 5 $\mu$m or less.

The pulverization time may be set several minutes or more and there is no particular upper limit. The longer the pulverization time is, the smaller the particle diameter of the boron compounds becomes and the smaller the maximum particle diameter becomes. However, when the pulverization time exceeds a certain length, the particle diameter converges and no further change is observed, and therefore, the pulverization may no longer be continued for further time when the particle diameter is considered to attain convergence, and the time may be set within a range, for example, of 10 minutes to 30 days.

The pulverization temperature is not particularly limited, and while some times the temperature of the boron compounds may rise by pulverizing, allowable temperature of the boron compounds is between −10° C. and up to the melting point of the boron compounds. Preferably, the temperature is 0 to 100° C. and more preferably 0 to 50° C.

When, in the kinds of the pulverizing machine, a pulverizing machine in which the pulverization is performed by giving vibration, for example, ball mill pulverizing machine, is used, one of conditions is the frequency of vibration of the container. The frequency of vibration is again not particularly limited and may be set depending on the performance of the pulverizing machine. For example, the frequency may be in the range of 100 times/minute to 100,000 times/minute When, in the kinds of the pulverizing machine, a pulverizing machine in which the pulverization is performed by using revolving hammers, for example hammer mill pulverizing machine, is used, one of conditions is the number of revolution of the hammer. The number of revolution is not particularly limited and may be set depending on the performance of the pulverizing machine, and for example, the frequency may be in the range of 100 times/minute to 100,000 times/minute.

When, in the kind of the pulverizing machine, a pulverizing machine in which the pulverization is performed by collision with each other of the substance in the steam of gas or liquid, for example jet mill pulverizing machine, the flow rate and the flow velocity of the gas or liquid used are not particularly limited, and the flow rate and the flow velocity can be anyone that allows to make the maximum particle diameter of the boron compounds of 50 $\mu$m or less: the flow rate may be, for example, within a range of 0.1 liter/second to 1,000 liter/second, and the flow velocity may be, for example, within a range of 0.1 meter/second to 1,000 meter/second.

The slurry concentration of a slurry of the boron compounds in the wet pulverization is not particularly limited, and the slurry concentration can be anyone that allows to make the maximum particle diameter of the boron compounds of 50 μm or less. The concentration may be, for example, 0.01 gram/liter to 1,000 grams/liter, preferably 0.1 gram/liter to 500 grams/liter and more preferably 1 gram/liter to 300 grams/liter.

The stable operation of and steady feed by the feeding apparatus can be realized by feeding the boron compound in the form of fine particles produced as above by the method feeding to a reactor in the state slurried in a solvent or by the method feeding in the state of powders. When used in the polymerization of olefins, the solvent usually used in the polymerization may be used as a solvent for slurrying, and there are illustrated aliphatic hydrocarbon solvents such as pentane, hexane, heptane, octane and the like, and unless the use does not cause problems, aromatic hydrocarbon solvents such as benzene, toluene, xylene and the like and halogenated hydrocarbon solvents such as chloroform, dichloromethane and the like, or others. When the boron compound in the form of fine particles is produced by wet pulverization, the solvent or dispersing medium for the slurry may be the used one.

When the feeding method of the present invention is

When the feeding method of the present invention is adopted in an apparatus for preparing a catalyst for olefin polymerization or in a reactor for olefin polymerization, or when the boron compound in the form of fine particles is used as a catalyst component for olefin polymerization, the catalyst for olefin polymerization includes a catalyst for olefin polymerization obtainable by using (A) a transition metal compound and (B) the above described boron compounds, or a catalyst for olefin polymerization obtainable by using (A) a transition metal compound, (B) the above described boron compounds and (C) an organoaluminum compound.

As the transition metal compound (A) herein, there can be used various compounds exhibiting activity for polymerization of olefins, and examples include metallocene complex and non-metallocene complex. Specific examples include biscyclopentadienyl zirconium dichloride, bis (methylcyclopentadienyl) zirconium dichloride, bis(n-butylcyclopentadienyl) zirconium dichloride, bis(tert-butylcyclopentadienyl) zirconium dichloride, bis (pentamethylcyclopentadienyl) zirconium dichloride, bis (trimethylsilylcyclopentadienyl) zirconium dichloride, ethylenebisindenyl zirconium dichloride, ethylenebis(4,5,6, 7-tetrahydroindenyl) zirconium dichloride, dimethylsilyl-bisindenyl zirconium dichloride, dimethylsilylbis(4,5,6,7-tetrahydroindenyl zirconium dichloride, dimethylsilylbis(2, 4-dimethylcyclopentadienyl) zirconium dichloride, zirconium dichloride, dimethylmethylene(cyclopentadienyl) (fluorenyl) zirconium dichloride, diphenylmethylene (cyclopentadienyl) (fluorenyl) zirconium dichloride, dimethylsilyl(tetramethylcyclopentadienyl) (tert-butylamido) zirconium dichloride, dimethylsilyl (tetramethylcyclopentadienyl) (3-tert-butyl-5-methyl-2-phenoxy) zirconium dichloride and the like, and compounds wherein zirconium in these compounds is changed to titanium, and further, compounds wherein dichloride in these compounds including the latter is changed to dimethyl or dibenzyl. Similarly, other examples include N,N'-bis(2, 6-diisopropylphenyl)-1,2-dimethylethylenediimino nickel dibromide, N,N'-bis(2,6-diisopropylphenyl)-1,2-dimethylethylenediimino palladium dibromide and the like.

As the organoaluminum compound (C), there can be used compounds having a carbon-aluminum bond in the molecule and generally used in the field of polymerization of olefins. Specific examples include trimethyl aluminum, triethyl aluminum, triisobutyl aluminum, methyl aluminoxane, isobutyl aluminoxane and the like.

As to the amounts to be used of respective catalyst components, it is desirable that respective components are used in a range of 0.1 to 10,000, preferably 5 to 2,000, in molar ratio of compound (C)/compound (A), and 0.01 to 100, preferably 0.5 to 10, in molar ratio of compound (B)/compound (A).

As monomers applicable to polymerization, any olefins having 2–20 carbon atoms can be used and two or more monomers can simultaneously be used. Specific examples of such olefins include linear olefins such as ethylene, propylene, butene-1, pentene-1, hexene-1, heptene-1, octene-1, nonene-1, decene-1 and the like, branched olefins such as 3-methylbutene-1, 3-methylpentene-1, 4-methylpentene-1, 2-methylpentene-1 and the like, and should not limited to the above described compounds. Specific examples of combination of monomers for copolymerization include ethylene and propylene, ethylene and butene-1, ethylene and hexene-1, ethylene and octene-1, propylene and butene-1 and the like, and should not limited to the above described combinations.

BEST MODE FOR CARRYING OUT THE INVENTION

The present invention will be described in more detail by means of Examples and Comparative Examples, but is not limited thereto.

Properties of polymers in Examples were measured by the methods described below.

(1) The density was measured according to JIS K-6760. Provided that the value of density (without annealing) was a value determined according to JIS K-6760 without the annealing treatment, and the value of density (with annealing) was a measured value after the annealing treatment.

(2) Content of α-olefin: It was measured from characteristic absorptions of ethylene and α-olefins using a infrared spectrophotometer (IR-810, manufactured by JASCO Corporation) and expressed by a number of short chain branches (SCB) per 1,000 carbon atoms.

(3) Melting point of copolymer: It was measured using Seiko SSC-5200 under the following conditions.

Heating: from 40° C. to 150° C. (10° C./minute), maintained for 5 minutes

Cooling: from 150° C. to 10° C. (5° C./minute), maintained for 10 minutes

Measurement: from 10° C. to 160° C. (5° C./minute)

(4) Intrinsic viscosity [η]: This was measured in a tetralin solution at 130° C. using Ubbelohde viscometer.

(5) Molecular weight and molecular weight distribution: they were measured with gel permeation chromatograph (150° C., manufactured by Waters) under the following conditions.

Column: TSK gel GMH-HT

Measuring temperature: 145° C., setting

Measuring concentration: 10 mg/10 ml o-dichlorobenzene (6) Melt flow rate (MFR) was measured at 190° C. according to the method provided under JIS K-6760.

(7) Particle diameter of boron compounds: it was determined by observing the boron compounds under an optical microscope and measuring the major axis in the image.

EXAMPLE 1
(Preparation of boron compound by precipitation)

Into a 500 ml cylindrical flask equipped with a stirrer and a thermometer was placed, at room temperature, 4.3 g of N,N'-dimethylanilinium tetrakis(pentafluorophenyl)borate (commercially available from Asahi Glass Company, maximum particle diameter: several millimeters), to which 290 ml of toluene was added. Then, the mixture was heated to 80° C. with stirring to completely dissolve N,N'-dimethylanilinium tetrakis(pentafluorophenyl)borate. On the other hand, 60 ml of hexane was placed in a 100 ml cylindrical flask equipped with a magnetic stirrer. To this was added 5 ml of the solution of N,N'-dimethylanilinium tetrakis(pentafluorophenyl)borate in toluene at 80° C. prepared above. Immediately, N,N'-dimethylanilinium tetrakis (pentafluorophenyl)borate precipitated in the form of fine particles. Their particle diameter observed under an optical microscope was 2–3 $\mu$m and no particle of 10 $\mu$m or more was observed.

EXAMPLE 2
(Preparation of boron compounds by precipitation)

Into a 500 ml cylindrical flask equipped with a stirrer and a thermometer was placed, at room temperature, 4.03 g of N,N'-dimethylanilinium tetrakis (pentafluorophenyl)borate (commercially available from Asahi Glass Company, maximum particle diameter: several millimeters), to which 339 ml of toluene was added. Then, the mixture was heated to 80° C. with stirring to completely dissolve N,N'-dimethylanilinium tetrakis(pentafluorophenyl)borate. On the other hand, 2205 g of hexane was placed in a 5-liter cylindrical flask equipped with a stirrer. To this was added the whole amount of the solution of N,N'-dimethylanilinium tetrakis(pentafluorophenyl)borate in toluene at 80° C. prepared above. Immediately, N,N'-dimethylanilinium tetrakis (pentafluorophenyl) borate precipitated in the form of fine particles. Their particle diameter was 2–3 $\mu$m and no particle of 10 $\mu$m or more was observed.

COMPARATIVE EXAMPLE 1

Into a 50 ml cylindrical flask equipped with a magnetic stirrer was placed, at room temperature, 2.0 g of N,N'-dimethylanilinium tetrakis(pentafluorophenyl)borate (commercially available from Asahi Glass Company, maximum particle diameter: several millimeters), to which 20 ml of acetone was added to completely dissolve N,N'-dimethylanilinium tetrakis(pentafluorophenyl)borate.

On the other hand, 500 g of water was placed in a 1 l cylindrical flask equipped with a stirrer at room temperature, stirring was carried out, and the whole amount of the solution of N,N'-dimethylanilinium tetrakis (pentafluorophenyl)borate in acetone prepared above. Immediately, N,N'-dimethylanilinium tetrakis (pentafluorophenyl) borate precipitated, but their shape were irregular and fine particles having a diameter of 1 $\mu$m or less, needle-like crystals of several tens $\mu$m and particles of several tens $\mu$m—several mm were observed.

EXAMPLE 3
(Dry pulverization)

Into a cylindrical metal container (metallic material: SUS316L) having an inner volume of 265 ml was placed about 350 g of metal spheres (material: SUS316L) having a diameter of about 5–6 mm, and 10.3 g of N,N'-dimethylanilinium tetrakis(pentafluorophenyl)borate (commercially available from Asahi Glass Company, maximum particle diameter: several millimeters) was added thereto. The container was sealed, placed in a small-scale vibration ball mill pulverizing machine (1042 Special Model, manufactured by Yoshida Seisakusho Co.) and subjected to pulverization at room temperature with vibrating at a vibration number of 1700/minute for 14 hours. 9.7 g of N,N'-dimethylanilinium tetrakis(pentafluorophenyl)borate in the form of fine particles were obtained. The recovery was 94.2%. The particle diameter was 2–3 $\mu$m and no particle of 10 $\mu$m or more was observed.

EXAMPLE 4
(Wet pulverization)

Into a cylindrical metal container (material: SUS316L) having an inner volume of 265 ml was placed about 370 g of metal spheres (material: SUS316L) having a diameter of about 5–6 mm, and 10.0 g of N,N'-dimethylanilinium tetrakis (pentafluorophenyl)borate (commercially available from Asahi Glass Company, maximum particle diameter: several millimeters) was added thereto, followed by addition of 100 ml of heptane. The container was sealed, placed in a small-scale vibration ball mill pulverizing machine (1042 Special Model, manufactured by Yoshida Seisakusho Co.) and subjected to pulverization at room temperature with vibrating at a vibration number of 1700/minute for 14 hours. There was obtained 9.7 g of N,N'-dimethylanilinium tetrakis (pentafluorophenyl)borate in the form of a slurry in heptane. The particle diameter was 2–3 $\mu$m and no particle of 10 $\mu$m or more was observed.

REFERENCE EXAMPLE
(Synthesis of transition metal compound: dimethylsilyl (tetramethylcyclopentadienyl) (3-tert-butyl-5-methyl-2-phenoxy) titanium dichloride)

(1) Synthesis of 1-bromo-3-tert-butyl-5-methyl-2-phenol

Under a nitrogen atmosphere, 20.1 (123 mmol) g of 2-tert-butyl-4-methylphenol was dissolved in 150 ml of toluene in a 500 ml 4-necked flask equipped with a stirrer, and subsequently 25.9 ml (18.0g, 246 mmol) of tert-butylamine was added thereto. The solution was cooled to −70° C. and 10.5 ml (32.6 g, 204 mmol) of bromine was added thereto. The solution was stirred for 2 hours keeping the solution at −70° C. Then, the solution was warmed back to room temperature and washed 3 times with addition of 100 ml of 10% diluted hydrochloric acid per one time. The organic layer obtained after washing was dried with anhydrous sodium sulfate, removing the solvent using an evaporator, purified with a silica gel column to give 18.4 g (75.7 mmol) of a colorless oil, 1-bromo-3-tert-butyl-5-methyl-2-phenol. The yield was 62%.

(2) Synthesis of 1-bromo-3-tert-butyl-2-methoxy-5-methylbenzene.

Under a nitrogen atmosphere, 13.9 g (57.2 mmol) of 1-bromo-3-tert-butyl-5-methyl-2-phenol synthesized in the above described (1) was dissolved in 40 ml of acetonitrile in a 100 ml 4-necked flask equipped with a stirrer and subsequently 3.8 g (67.9 mmol) of potassium hydroxide was added thereto. Further, 17.8 ml (40.6 g, 286mmol) of methyl iodide was added and the mixture was stirred for 12 hours. Then, the solvent was removed by an evaporator and the residue was treated with 40 ml of hexane to extract hexane soluble fraction. The extraction was repeated three times. The solvent was removed from the extracts to give 13.8 g (53.7 mmol) of a pale yellow oil, 1-bromo-3-tert-butyl-2-methoxy-5-methylbenzene. The yield was 94%.

(3) Synthesis of (3-tert-butyl-2-methoxy-5-methylphenyl) chlorodimethylsilane

To a solution consisting of tetrahydrofuran (31.5ml), hexane (139 ml) and 1-bromo-3-tert-butyl-2-methoxy-5-methylbenzene (45 g) synthesized in the above described (2) was added dropwise a 1.6 mol/liter solution (115 ml) of n-butyl lithium in hexane at −40° C. over 20 minutes. The obtained mixture was kept at −40° C. for 1 hour and tetrahydrofuran (31.5 ml) was added dropwise thereto.

To a solution consisting of dichlorodimetylsilane (131 g) and hexane (306 ml) was added dropwise the mixture obtained above at −40° C. The obtained mixture was warmed to room temperature during 2 hours and stirred further at room temperature for 12 hours.

The solvent and excess dichlorodimetylsilane were evaporated from the reaction mixture under reduced pressure, a hexane soluble fraction was extracted from the residue with hexane, and the solvent was evaporated from the obtained hexane solution to give 41.9 g of a pale yellow oil, (3-tert-butyl-2-methoxy-5-methylphenyl) chlorodimethyl silane. The yield was 84%.

(4) Synthesis of (3-tert-butyl-2-methoxy-5-methylphenyl) dimethyl(tetramethylcyclopentadienyl)silane To a solution consisting of (3-tert-butyl-2-methoxy-5-methylphenyl)chlorodimethylsilane (5.24 g) synthesized in the above described (3) and tetrahydrofuran (50 ml) was added tetramethylcyclopentadienyl lithium (2.73 g) at −35° C., and the mixture was warmed to room temperature during 2 hours and stirred further at room temperature for 10 hours.

The solvent was evaporated from the reaction mixture under reduced pressure, a hexane soluble fraction was extracted from the residue with hexane, and the solvent was evaporated from the obtained hexane solution to give 6.69 g of a yellow oil of (3-tert-butyl-2-methoxy-5-methylphenyl) dimethyl(tetramethylpentdienyl)silane. The yield was 97%.

(5) Synthesis of dimethylsilyl(tetramethyl-cyclopentadienyl)(3-tert-butyl-5-methyl-2-phenoxy) titanium dichloride To a solution consisting of (3-tert-butyl-2-5 methoxy-5-methylphenyl)dimethyl(tetramethylpentdienyl)silane (10.04 g) synthesized in the above described (4), toluene (100 ml) and triethylamine (6.30 g) was added dropwise a 1.63 mol/liter solution (19.0 ml) of n-butyl lithium in hexane 10 at −70° C., and then the obtained mixture was warmed to room temperature over 2 hours and stirred further at room temperature for 12 hours.

The mixture obtained above was added dropwise to a solution of titanium tetrachloride (4.82 g) in toluene (50 ml) at 0° C. under a nitrogen atmosphere, and then the obtained mixture was warmed to room temperature over 1 hour and stirred further at room temperature for 10 hours.

The reaction mixture was filtered, the solvent was evaporated from the filtrate and the residue was recrystallized from a mixed solvent of toluene/hexane to give 3.46 g of orange prisms-like crystal of dimethylsilyl (tetramethylcyclopentadienyl) (3-tert-butyl-5-methyl-2-phenoxy) titanium dichloride. The yield was 27%.

The spectral data were as follows.
$^1$H-NMR (CDCl$_3$), δ0.57 (s, 6H), 1.41 (s, 9H), 2.15 (s, 6H), 2.34 (s, 6H), 2.38 (s, 3H), 7.15 (s, 1H), 7.18 (s, 1H)
$^{13}$C-NMR (CDCl$_3$), δ: 1.25, 14.48, 16.28, 22.47, 31.25, 36.29, 120.23, 130.62, 131.47, 133.86, 135.50, 137.37, 140.82, 142.28, 167.74
MS (CI, m/e): 458

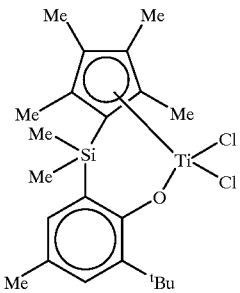

EXAMPLE 5

Polymerization was carried out using an autoclave type reactor having an inner volume of 1 liter and equipped with stirring blades by continuously feeding ethylene and butene-1 into the reactor. In the conditions for polymerization, the total pressure was set at 800 kg/cm$^2$G, the concentration of butene-1 at 29% by mol and the concentration of hydrogen at 0.12% by mol. In separate containers were prepared a solution of dimethylsilyl (tetramethylcyclopentadienyl)(3-tert-butyl-5-methyl-2-phenoxy) titanium dichloride in hexane (0.7 μmol/g), a solution of triisobutyl aluminum in heptane (35 μmol/g) and further a dispersion of N,N-dimethylanilinium tetrakis (pentafluorophenyl) borate (fine-granulated by the precipitating method using toluene and heptane. The particle diameter was 2–3 μm and no particle of 10 μm or more was observed. 1.2 μmol/g) in a mixed solution (volume ratio of heptane: liquid paraffin =1:4) of heptane and liquid paraffin (Crystol 202, manufactured by Esso Sekiyu K.K., viscosity= 130 cp at 18° C.), and each of them was continuously fed to the reactor through a pipeline having a diameter of 3.175 mm at a feeding rate of 300 g/hour, 360 g/hour and 750 g/hour, respectively. The temperature of polymerization was controlled to 230° C., the molar ratio of Al atom to Ti atom to 60 and the ratio of boron atom to Ti atom to 4.4. As the result, ethylene-butene-1 copolymer having a melting point of 90.6° C., a molecular weight (Mw) of 64,000 and a molecular weight distribution (Mw/Mn) of 1.7 was produced at a rate of 10 ton per 1 mol of Ti atom per 1 hour.

EXAMPLE 6

Polymerization was carried out using an autoclave type reactor having an inner volume of 1 liter and equipped with stirring blades by continuously feeding ethylene and butene-1 into the reactor. In the conditions for polymerization, the total pressure was set at 800 kg/cm$^2$G and the concentration of butene-1 at 45.9% by mol. Dimethylsilyl (tetramethylcyclopentadienyl) (3-tert-butyl-5-methyl-2-phenoxy) titanium dichloride (0.066 μmol/g) was dissolved in a mixed solution (volume ratio of heptane:liquid paraffin=1:4) of heptane and liquid paraffin (Crystol 202, manufactured by Esso Sekiyu K.K.) and N,N-dimethylanilinium tetrakis(pentafluorophenyl)borate (fine-granulated by the precipitating method using toluene and heptane. The particle diameter was 2–3 μm and no particle of 10 μm or more was observed.) was dispersed (0.4 μmol/g) controlling such that the ratio of boron atom and Ti atom was 6.0. In separate containers were prepared the mixed dispersion-solution and a solution of triisobutyl aluminum in heptane (5.47 μmol/g), and each of them was continuously fed to the reactor through a pipeline having a diameter of 3.175 mm at a feeding rate of 323 g/hour and 240 g/hour, respectively. The temperature of polymerization was controlled to 205° C. and the molar ratio of Al atom and Ti atom to 61.7. As the result, ethylene-butene-1 copolymer having a density (without annealing) of 0.873 g/cm$^3$, a MFR of 6.8 g/10 minutes, a molecular weight (Mw) of 72,000 and a molecular weight distribution (Mw/Mn) of 1.7 was produced at a rate of 98.4 ton per 1 mol of Ti atom per 1 hour.

EXAMPLE 7

Polymerization was carried out using an autoclave type reactor having an inner volume of 1 liter and equipped with stirring blades by continuously feeding ethylene and butene-1 into the reactor. In the conditions for polymerization, the total pressure was set at 800 kg/cm$^2$G and the concentration of butene-1 at 47.0% by mol. Dimethylsilyl (tetramethylcyclopentadienyl) (3-tert-butyl-5-methyl-2-phenoxy) titanium dichloride (0.066 μmol/g) was dissolved in a mixed solution (in a volume ratio of heptane:liquid paraffin=1:4) of heptane and liquid paraffin (Crystol 202, manufactured by Esso Sekiyu K.K.) and N,N-dimethylanilinium tetrakis(pentafluorophenyl)borate (fine-granulated by the precipitating method using toluene and heptane. The particle diameter was 2–3 $\mu$m and no particle of 10 $\mu$m or more was observed.) was dispersed (0.4 $\mu$mol/g) controlling such that the ratio of boron atom to Ti atom was6.0. In separate containers were prepared the mixed dispersion-solution and a solution of triisobutyl aluminum in heptane (5.47 $\mu$mol/g), and each of them was continuously fed to the reactor through a pipeline having a diameter of 3.175 mm at a feeding rate of 373 g/hour and 283 g/hour, respectively. The temperature of polymerization was controlled to 206° C. and the molar ratio of Al atom and Ti atom to 63.3. As the result, ethylene-butene-1 copolymer having a density (without annealing) of 0.867 g/cm$^3$, a melting point of 42.6° C. and a MFR of 11.8 g/10 minutes was produced at a rate of 106.3 ton per 1 mol of Ti atom per 1 hour.

EXAMPLE 8

Polymerization was carried out using an autoclave type reactor having an inner volume of 1 liter and equipped with stirring blades by continuously feeding ethylene and butene-1 into the reactor. In the conditions for polymerization, the total pressure was set at 800 kg/cm$^2$G and the concentration of butene-1 at 43.9% by mol.

Dimethylsilyl (tetramethylcyclopentadienyl) (3-tert-butyl-5-methyl-2-phenoxy) titanium dichloride (0.066 $\mu$mol/g) was dissolved in a mixed solution (volume ratio of heptane:liquid paraffin=1:4) of heptane and liquid paraffin (Crystol 202, manufactured by Esso Sekiyu K.K.) and N,N-dimethylanilinium tetrakis(pentafluorophenyl)borate (fine-granulated by the precipitating method using toluene and heptane. The particle diameter was 2–3 $\mu$m and no particle of 10 $\mu$m or more was observed.) was dispersed (0.4 $\mu$mol/g) controlling such that the ratio of boron atom and Ti atom was 6.0. In separate containers were prepared the mixed dispersion-solution and a solution of triisobutyl aluminum in heptane (5.47 $\mu$mol/g), and each of them was continuously fed to the reactor through a pipeline having a diameter of 3.175 mm at a feeding rate of 290 g/hour and 270 g/hour, respectively. The temperature of polymerization was controlled to 205° C. and the molar ratio of Al atom and Ti atom to 77.2. As the result, ethylene-butene-1 copolymer having a MFR of 13.3 g/10 minutes was produced at a rate of 104.5 ton per 1 mol of Ti atom per 1 hour.

EXAMPLE 9

Polymerization was carried out using an autoclave type reactor having an inner volume of 1 liter and equipped with stirring blades by continuously feeding ethylene and hexene-1 into the reactor. In the conditions for polymerization, the total pressure was set at 796 kg/cm$^2$G and the concentration of hexene-1 at 29.7% by mol. In separate containers were prepared a solution of dimethylsilyl (tetramethylcyclopentadienyl) (3-tert-butyl-5-methyl-2-phenoxy) titanium dichloride mixed with triisobutyl aluminum in heptane (the concentrations of said complex and triisobutyl aluminum being 0.37 $\mu$mol/g and 18.5 $\mu$mol/g, respectively, and the molar ratio of Al atom to Ti atom being 50) and further a dispersion (0.71 $\mu$mol/g) of N,N-dimethylanilinium tetrakis(pentafluorophenyl)borate fine-granulated by the wet pulverizing method (the maximum particle diameter: 20 $\mu$m or less) in a mixed solution (volume ratio of heptane liquid paraffin 1:4) of heptane/liquid paraffin (Crystol 202, manufactured by Esso Sekiyu K.K.), and each of them was continuously fed to the reactor through a pipeline having a diameter of 3.175 mm at a feeding rate of 246 g/hour and 484 g/hour, respectively. The temperature of polymerization was controlled to 210° C., and the ratio of boron atom to Ti atom to 3.6. As the result, ethylene-hexene-1 copolymer having a MFR of 3.8 g/10 minutes, a density (without annealing) of 0.889 g/cm$^3$ was produced at a rate of 28 ton per 1 mol of Ti atom per 1 hour.

EXAMPLE 10

Polymerization was carried out using an autoclave type reactor having an inner volume of 1 liter and equipped with stirring blades by continuously feeding ethylene and hexene-1 into the reactor. In the conditions for polymerization, the total pressure was set at 796 kg/cm$^2$G and the concentration of hexene-1 at 31.6% by mol. In separate containers were prepared a solution of dimethylsilyl (tetramethylcyclopentadienyl)(3-tert-butyl-5-methyl-2-phenoxy) titanium dichloride mixed with triisobutyl aluminum in heptane (the concentrations of said complex and triisobutyl aluminum being 2 $\mu$mol/g and 200 $\mu$mol/g, respectively, and the molar ratio of Al atom to Ti atom being 100) and further a dispersion (7.0 $\mu$mol/g) of N,N-dimethylanilinium tetrakis(pentafluorophenyl)borate fine-granulated by the wet pulverizing method (the maximum particle diameter: 20 $\mu$m or less) in liquid paraffin (a mixture of Crystol 202, manufactured by Esso Sekiyu K.K. (viscosity=130 cp at 18° C.) and IP Solvent 2028, manufactured by Idemitsu Petrochemical Co., Ltd. (viscosity=3.2 cp at 19° C.), Crystol 202:IP Solvent 2028=60:40 (% by volume)), and each of them was continuously fed to the reactor through a pipeline having a diameter of 3.175 mm at a feeding rate of 90 g/hour and 195 g/hour, respectively. The temperature of polymerization was controlled to 220° C., and the ratio of boron atom to Ti atom to 7.6. As the result, ethylene-hexene-1 copolymer having a MFR of 5.8 g/10 minutes, a density (with out annealing) of 0.888 g/cm$^3$, a melting point of 69.8° C. and a SCB of 32.6 was produced at a rate of 11 ton per 1 mol of Ti atom per 1 hour.

EXAMPLE 11

Polymerization was carried out using an autoclave type reactor having an inner volume of 1 liter and equipped with stirring blades by continuously feeding ethylene and hexene-1 into the reactor. In the conditions for polymerization, the total pressure was set at 796 kg/cm$^2$G and the concentration of hexene-1 of 31.1% by mol. In separate containers were prepared a solution of dimethylsilyl (tetramethylcyclopentadienyl) (3-tert-butyl-5-methyl-2-phenoxy) titanium dichloride mixed with triisobutyl aluminum in heptane (the concentrations of said complex and triisobutyl aluminum being 0.37 $\mu$mol/g and 18.5 $\mu$mol/g, respectively, and the molar ratio of Al atom to Ti atom being 50) and further a dispersion (1.39 $\mu$mol/g) of N,N-dimethylanilinium tetrakis(pentafluorophenyl)borate fine-granulated by the wet pulverizing method (the maximum particle diameter: 20 $\mu$m or less) in liquid paraffin (a 60:40 (% by volume) mixture of Crystol 202, manufactured by Esso Sekiyu K.K. and IP solvent 2028, manufactured by Idemitsu Petrochemical Co., Ltd.), and each of them was continuously fed to the reactor through a pipeline having a diameter of 3.175 mm at a feeding rate of 745 g/hour and 1235 g/hour, respectively. The temperature of polymerization was controlled to 247° C., and the ratio of boron atom to Ti atom to 6.22. As the result, ethylene-hexene-1 copolymer having a MFR of 55 g/10 minutes, a density (without annealing) of 0.886 g/cm$^3$ was produced at a rate of 13 ton per 1 mol of Ti atom per 1 hour.

INDUSTRIAL APPLICABILITY

As described above in detail, according to the present invention, there is provided a method which is capable of feeding a boron compound useful as a catalyst component for olefin polymerization continuously and in a large amount to a reactor, and particularly, it enables continuous feed in a large amount of said boron compound to an apparatus for compounding catalyst for olefin polymerization or a reactor for olefin polymerization. In addition, according to the present invention, a boron compound in the form of fine particles and a method for producing it are provided. Said boron compound in the form of fine particles is capable of allowing steady feed thereof without using it in the state of solution, and allowing stable operation of a feeding apparatus, for example, a high-pressure pump, when used in an industrial manufacturing apparatus, for example, in a reactor for olefin polymerization, and thus the value in utilization of the present invention is extremely great.

What is claimed is:

1. A method for feeding a boron compound comprising feeding at least one boron compound selected from the group consisting of (1), (2) and (3) described below in the state of which the boron compound is suspended or slurried in a solvent continuously to a reactor:

(1) a boron compound represented by the general formula: $BQ^1Q^2Q^3$;

(2) a boron compound represented by the general formula: $G^+(BQ^1Q^2Q^3Q^4)^-$; and (3) a boron compound represented by the general formula: $(L-H)^+(BQ^1Q^2Q^3Q^4)^-$ in each of the above general formulae, B is a boron atom in the trivalent valence state, $Q^1$ to $Q^4$ are a halogen atom, a hydrocarbon group, a halogenated hydrocarbon group, a substituted silyl group, an alkoxy group or a di-substituted amino group, which may be the same or different, respectively, $G^+$ is an inorganic or organic cation, L is a neutral Lewis base, and $(L-H)^+$ is a Brønsted acid.

2. The method for feeding a boron compound according to claim 1, wherein the solvent is a hydrocarbon solvent.

3. The method for feeding a boron compound according to claim 2, wherein the hydrocarbon solvent is a saturated hydrocarbon solvent.

4. The method for feeding a boron compound according to claim 1, wherein the solvent is a solvent having a viscosity of 0.8 cp or more.

5. The method for feeding a boron compound according to any of claims 1 to 4, wherein the reactor is an apparatus for compounding catalyst or a reactor for olefin polymerization.

6. The method for feeding a boron compound according to anyone of claims 1 to 4, wherein the reactor is a reactor for olefin polymerization.

7. The method for feeding a boron compound according to claim 6, wherein the reactor for olefin polymerization is a reactor for olefin polymerization by high-pressure ionic polymerization method.

8. The method for feeding a boron compound according to claim 7, wherein the reactor for olefin polymerization is a reactor for olefin polymerization in which the polymerization is carried out under a pressure of at least 300 kg/cm$^2$G and a temperature of at least 130° C.

9. The method for feeding a boron compound according to anyone of claims 1 to 4, wherein the boron compound has a maximum particle diameter of 50 μm or less.

10. A boron compound in the form of fine-particles, comprising being one or more boron compounds selected from the group consisting of (1), (2) and (3) described below and having a maximum particle diameter of 50 μm or less:

(1) a boron compound represented by the general formula: $BQ^1Q^2Q^3$:

(2) a boron compound represented by the general formula: $G^+(BQ^1Q^2Q^4)^-$; and (3) a boron compound represented by the general formula: $(L-H)^+(BQ^1Q^2Q^3Q^4)^-$, in each of the above general formulae, B is a boron atom in the trivalent valence state, $Q^1$ to $Q^4$ are a halogen atom, a hydrocarbon group, a halogenated hydrocarbon group, a substituted silyl group, an alkoxy group or a di-substituted amino group, which may be the same or different, respectively, $G^+$ is an inorganic or organic cation, L is a neutral Lewis base, and $(L-H)^+$ is a Brønsted acid.

11. A boron compound in the form of fine particles obtained by a process comprising dissolving one or more boron compounds selected from the group consisting of (1), (2) and (3) described below in an aromatic hydrocarbon solvent and then precipitating in an aliphatic hydrocarbon solvent to obtain fine particles of the boron compound having a maximum particle diameter of 50 μm or less:

(1) a boron compound represented by the general formula: $BQ^1Q^2Q^3$, (2) a boron compound represented by the general formula: $G^+(BQ^1Q^2Q^3Q^4)^-$, and (3) a boron compound represented by the general formula: $(L-H)^+(BQ^1Q^2Q^3Q^4)^-$, in each of the above general formulae, B is a boron atom in the trivalent valence state, $Q^1$ to $Q^4$ are a halogen atom, a hydrocarbon group, a halogenated hydrocarbon group, a substituted silyl group, an alkoxy group or a di-substituted amino group, which may be the same or different, respectively, $G^+$ is an inorganic or organic cation, L is a neutral Lewis base, and $(L-H)^+$is a Brønsted acid.

12. The boron compound in the form of fine particles according to claim 10 or 11, wherein $Q^1$ to $Q^4$ are respectively a fluorinated hydrocarbon group of 1 to 20 carbon atoms.

13. The boron compound in the form of fine particles according to claim 10 or 11, wherein $Q^1$ to $Q^4$ are respectively a fluorinated aryl group of 6 to 20 carbon atoms.

14. The boron compound in the form of fine particles according to claim 10 or 11, wherein the boron compound is tris(pentafluorophenyl) borane, triphenylmethyl tetrakis(pentafluorophenyl)borate, tri-n-butylammonium tetrakis(pentafluorophenyl)borate or N,N-dimethylanilinium tetrakis(pentafluorophenyl)borate.

15. A catalyst component for olefin polymerization consisting the boron compound in the form of fine particles according to claim 10 or 11.

16. A method for producing a boron compound in the form of fine particles, comprising dissolving one or more boron compounds selected from the group consisting of (1), (2) and (3) described below in an aromatic hydrocarbon solvent and then precipitating in an aliphatic hydrocarbon solvent:

(1) a boron compound represented by the general formula: $BQ^1Q^2Q^3$;

(2) a boron compound represented by the general formula: $G^+(BQ^1Q^2Q^3Q^4)$: and (3) a boron compound represented by the general formula: $(L-H)^+(BQ^1Q^2Q^3Q^4)^-$, in each of the above general formulae, B is a boron atom in the trivalent valence state, $Q^1$ to $Q^4$ are a halogen atom, a hydrocarbon group, a halogenated hydrocarbon group, a substituted silyl group, an alkoxy group or a di-substituted amino group, which may be the same or different, respectively, $G^+$ is an inorganic or organic cation, L is a neutral Lewis base, and $(L-H)^+$ is a Brønsted acid.

17. A method for producing a boron compound in the form of fine particles, comprising pulverizing one or more boron compounds selected from the group consisting of (1), (2) and (3) described below so that their maximum particle diameter is 50 μm or less, (1) a boron compound represented by the general formula: $BQ^1Q^2Q^3$:

(2) a boron compound represented by the general formula: $G^+(BQ^1Q^2Q^3Q^4)^-$ and (3) a boron compound represented by the general formula: $(L-H)^+(BQ^1Q^2Q^3Q^4)^-$ in each of the above general formulae, B is a boron atom in the trivalent valence state, $Q^1$ to $Q^4$ are a halogen atom, a hydrocarbon group, a halogenated hydrocarbon group, a substituted silyl group, an alkoxy group or a di-substituted amino group, which may be the same or different, respectively, $G^+$ is an inorganic or organic cation, L is a neutral Lewis base, and $(L-H)^+$ is a Brønsted acid.

18. The method for producing a boron compound in the form of fine particles according to claim 17, wherein the pulverization is dry pulverization or wet pulverization.

19. The method for producing the boron compound in the form of fine particles according to claim 18, wherein the wet pulverization is carried out in an aliphatic hydrocarbon solvent.

20. The method for producing the boron compound in the form of fine particles according to any of claims 16 to 19, wherein $Q^1$ to $Q^4$ are respectively a fluorinated hydrocarbon group of 1 to 20 carbon atoms.

21. The method for producing the boron compound in the form of fine particles according to claim 20, wherein $Q^1$ to $Q^4$ are respectively a fluorinated aryl group of 6 to 20 carbon atoms.

22. The method for producing boron compound in the form of fine particles according to claim 16, wherein the boron compound is tris(pentafluorophenyl) borane, triphenylmethyl tetrakis(pentafluorophenyl)borate, tri-n-butylammonium tetrakis(pentafluorophenyl)borate or N,N-dimethylanilinium tetrakis(pentafluorophenyl)borate.

23. The boron compound in the form of fine particles according to claim 10, which has a maximum particle diameter of 10 μm or less.

* * * * *